US006902671B2

(12) United States Patent
Cappia et al.

(10) Patent No.: US 6,902,671 B2
(45) Date of Patent: Jun. 7, 2005

(54) CHEMICAL PROCESS SYSTEM WITH MULTI-FUNCTIONAL BARRIER FILTER

(75) Inventors: Jean-Marc Cappia, Saint Maur (FR); Stephen Proulx, Boxboro, MA (US); Stephen Tingley, North Reading, MA (US); Jack Messing, Townsend, MA (US); Matthias Gratzfeld, Ranschbach (DE)

(73) Assignee: Millipore Corporation, Billerica, MA (US)

( * ) Notice: Subject to any disclaimer, the term of this patent is extended or adjusted under 35 U.S.C. 154(b) by 23 days.

(21) Appl. No.: 10/011,676

(22) Filed: Dec. 3, 2001

(65) Prior Publication Data

US 2002/0096467 A1 Jul. 25, 2002

Related U.S. Application Data

(60) Provisional application No. 60/250,436, filed on Dec. 1, 2000.

(51) Int. Cl.[7] .......................................... B01D 63/00
(52) U.S. Cl. ........................... 210/257.2; 210/321.64; 210/321.77; 210/321.86; 210/493.1; 210/346; 210/433.1; 210/472; 96/6
(58) Field of Search ................... 210/321.64, 321.75, 210/321.76, 321.77, 321.84, 346, 433.1, 435, 506, 493.5, 504, 767, 314, 315, 321.85; 264/48, 49; 95/45, 47, 51, 52, 54; 96/4, 6, 7, 9, 11; 55/308, 318, 321, 322, 324, 482, 484, 485

(56) References Cited

U.S. PATENT DOCUMENTS

| 4,302,223 A | 11/1981 | Booth et al. .................. 55/158 |
| 4,459,139 A | 7/1984 | von Reis et al. ............. 55/189 |
| 4,571,244 A | 2/1986 | Knighton ..................... 604/118 |
| 4,863,603 A | * 9/1989 | Lehmann et al. ........... 210/489 |
| 5,055,198 A | * 10/1991 | Shettigar .................... 210/650 |
| 5,779,674 A | 7/1998 | Ford .......................... 604/126 |
| 5,902,490 A | * 5/1999 | Zuk, Jr. ...................... 210/767 |
| 5,928,516 A | * 7/1999 | Hopkins et al. ............ 210/636 |
| 5,980,759 A | 11/1999 | Proulx et al. ............... 210/767 |

FOREIGN PATENT DOCUMENTS

| DE | 2844073 | 4/1980 | .......... B01D/35/00 |
| DE | 4219966 | 1/1993 | .......... B01D/29/05 |
| DE | 4319458 | 12/1993 | .......... A16M/16/10 |
| EP | 0081655 | 6/1983 | ............ A61M/1/00 |
| JP | 01007907 A | * 1/1989 | .......... B01D/13/00 |
| JP | 5161827 | 6/1993 | .......... B01D/81/18 |

OTHER PUBLICATIONS

PCT International Search Report for PCT/US01/47425 (Form PCT/ISA/210)(mailed Aug. 16, 2002).
Patent Abstracts of Japan, EPO vol. 1997, No. 01, Jan. 31, 1997.

* cited by examiner

*Primary Examiner*—W. L. Walker
*Assistant Examiner*—K S Menon
(74) *Attorney, Agent, or Firm*—Renato M. de Luna

(57) ABSTRACT

A barrier filter useful for aseptically discharging both gaseous and liquid fluids from a chemical process system is disclosed The barrier filter comprises, within a common enclosure, one or several filter membranes having singularly or collectively a mixture or hydrophobic and hydrophilic regions. The common enclosure of the barrier filter is provided with a fluid inlet and a fluid outlet. All filter membranes are located within the fluid path between the fluid inlet and the fluid outlet. A variety of membrane-based systems, into which such barrier filter is installed, are also disclosed.

8 Claims, 8 Drawing Sheets

CHEMICAL PROCESS SYSTEM WITH MULTI-FUNCTIONAL BARRIER FILTER

REFERENCE TO RELATED APPLICATION

This application claims the benefit of Provisional U.S. Pat. App. Ser. No. 60/250,436, filed Dec. 1, 2000.

FIELD

In general, the present invention is directed to a barrier filter unit and, in particular, to an aseptic barrier filter unit having regionally defined gas and liquid permeability.

BACKGROUND

During the manufacture of pharmaceuticals, for example, assuring and maintaining sterility of the process is critical. For aqueous processes, a sterile process filter unit (containing membrane material) is often placed within the process system to filter the effluent sent ultimately to a collection vessel. Steam is often used to sterilize both the product and the process equipment. However, steam can damage the process filter unit's membrane components, compromising the sterility of the system. Integrity testing of the process filter thus becomes necessary to ensure that it is operational.

Integrity testing involves flowing liquid, usually water, through the process filter to wet the membrane material therein. Once the process membrane material is wet, the water must be removed from the system. This typically requires a drain valve through which the water from the wet first filter is removed. In typical conventional systems, this valve is not protected by any microbial barrier, and therefore, is a potential point of contamination of the now sterile system. Air borne microbes can enter the system through the valve when opened for drainage.

The second step of the integrity test is to pressurize the system with a gas, usually air or nitrogen. Again, however, the gas must be exhausted upon completion.

The use of water and air in the integrity testing, and the subsequent removal of each from the filter, is problematic in conventional membrane-based fluid processing systems. The process filters used therein typically employ either hydrophobic or hydrophilic process membrane material and thus would seem to compel the resource-intensive identification, selection, and installation of a vent filter from a limited range of compatible matching discharge vent filter types. Off-line testing of the filter has been one solution to this problem, but is inefficient and costly, and doesn't ensure sterile integrity of the previously sterilized system.

It would therefore be desirable to provide a filter which allows for the use of both a hydrophilic and hydrophobic medium for integrity testing and to allow for the removal of unwanted gas or liquid from the system while maintaining a sterile barrier to the system against microbial contamination.

SUMMARY

In response to the aforementioned needs, the present invention provides a filter comprising, within a common enclosure, one or several filter membranes having singularly or collectively a mixture or hydrophobic and hydrophilic regions, the common enclosure having a fluid inlet, a fluid outlet, and a fluid path therebetween, all filter membranes being located within the fluid path. Several embodiments are envisioned. For example, the filter can be configured as a so-called "process scale cartridge" or "capsule filter device" provided with wrapped, wound, or stacked hydrophobic and hydrophilic membrane material. The use of hydrophilic and hydrophobic membrane material within a single filter unit effectively enables a balanced combination of good gas and liquid filtration functionality.

The inventive filter unit can be employed in several applications, paramount among which, is its inventive use as a barrier filter in a membrane-based process (e.g., filtration, isolation, purification, etc.) for manufacturing a liquid product (e.g., a pharmaceutical grade antibody) from a liquid raw material (e.g., a raw incubated antibody culture). In such chemical process, a network of conduits and receptacles are assembled to define a desired fluid process stream, wherein liquid raw material is introduced at one end of the stream and withdrawn as liquid product at another end. Process membrane(s) are positioned within the fluid process stream. The barrier filter is installed between a process membrane and an end of the fluid process stream where liquid product is collected. At this location the barrier filter can be used for the aseptic discharge of fluids—both gas and liquid—run through the system, for example, for cleaning and/or integrity testing of the process membranes.

Use of the inventive barrier filter can yield several advantages. For example, post "steam-in-place" and drying of aseptic processing equipment without undesirably compromising the sterility of the system is achievable. Also, the combined hydrophilic/hydrophobic properties of the barrier filter reduces product dilution resultant of residual condensation after "steam-in-place" processes. Also, pre-flushing a chemical process system with water can be accomplished effectively and aseptically. Also, comparatively large volume of liquid can be used for removal of extractables and for pre-wetting for integrity testing. The filter, according to one embodiment thereof, can be integrity tested with a 70/30 mixture of isopropyl alcohol and water.

In light of the above, it is a principal object of the present invention filter unit capable of effectively filtering both liquid and gaseous fluids.

It is another object of the present invention to provide a filter unit comprising, within a common enclosure, one or several filter membranes having singularly or collectively a mixture or hydrophobic and hydrophilic regions.

It is another object of the present invention to provide a means for aseptically discharging gaseous and liquid fluids conducted through a membrane-based chemical process system in the course of testing the integrity of the process membranes used therein.

For further understanding of the nature and objects of the invention, reference should be had to following description considered in conjunction with the accompanying drawings.

BRIEF DESCRIPTION OF THE DRAWINGS

Each of FIGS. 1 to 9 provides a schematic representational illustration. The relative location, shapes, and sizes of certain objects are occasionally exaggerated to facilitate discussion and presentation herein.

DETAILED DESCRIPTION

Figure 1:
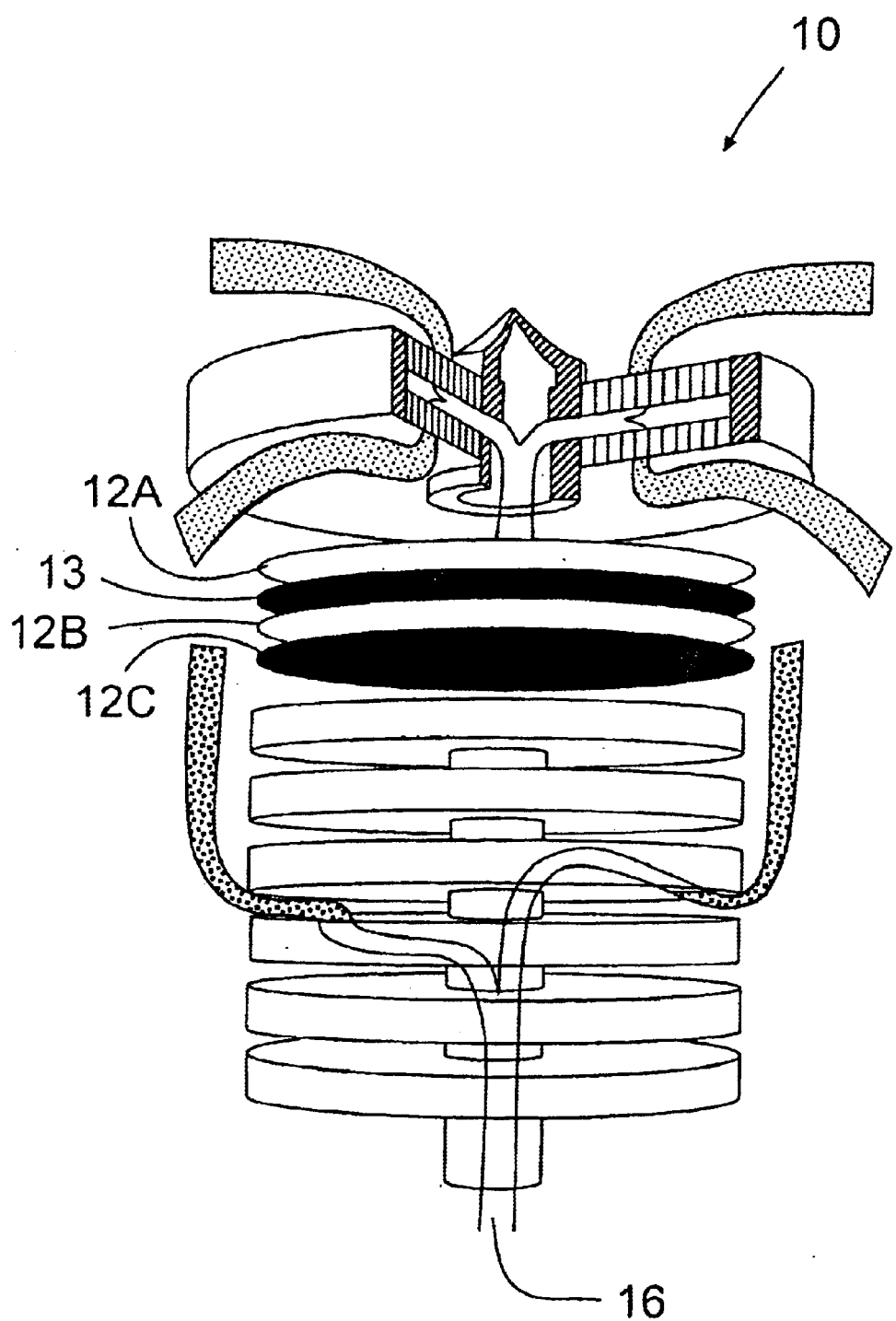
FIG. 1 is an isometric view, partially in section, of a stacked disc design filter in accordance with one embodiment of the present invention.

The present invention is drawn to a filter unit having a combination of hydrophilic and hydrophobic membrane regions and to a chemical process system into which said filter unit is installed. The inventive filter unit is configured to provide a sterile barrier at fluid discharge points in aseptic pharmaceutical/chemical processes, enabling liquid and/or gas withdrawal, yet maintaining the sterile conditions under which the process is conducted. In membrane-based chemical processes (e.g., product purification, concentration, and isolation processes), fluid withdrawal is often conducted, for example, during and after steam sterilization, for drying and cooling of aseptic processing equipment, and for pre-use integrity testing of membrane filters.

In respect of its structural configuration, the inventive filter comprises, within a common enclosure (e.g., a filter housing, casing, or the like), one or several filter membranes having singularly or collectively a mixture or hydrophobic and hydrophilic regions. The common enclosure is provided with a fluid inlet, a fluid outlet, and a fluid path therebetween. All of the filter membranes enclosed within the housing are located within said fluid path.

The common enclosure of the inventive filter, as evident from the product embodiments discussed further below, can be structured in various formats and dimensions, employing a variety of materials. Common formats include, but are not limited to, box-like cassettes, disks, and long or squat cylinders. Such formats are well-known in the art. See e.g., U.S. Pat. No. 5,980,759, issued to S. Proulx et al. on Nov. 9, 1999; U.S. Pat. No. 5,006,235, issued to R. B. Cooper on Apr. 9, 1991; U.S. Pat. No. 6,153,098, issued to R. E. Bayerlein et al. on Nov. 28, 2000; and U.S. Pat. No, 6,123,078, issued to K. A. Roberts et at, on Sep. 26, 2000.

It is preferred that the common enclosure be structured such that, but for the enclosure's inlet and outlet, the internal volume contained thereby is essentially "closed".

The enclosure's inlet and outlet, in combination with the filter's internal structure, will determine the process stream through which fluid is conducted through the filter. The filter membrane component of the filters can be positioned within the process stream in several arrangements. For example, the membrane components can be positioned tangentially or orthogonally along the process stream. The membrane component may be either a singular unit (e.g., a pleated tubular membrane) or a plurality of individual units (e.g., a stack of individual membrane disks).

The inventive filter can be constructed using any of several commercially-available or otherwise publicly-accessible membranes or membrane technologies. A preferred membrane material is hydrophobic polyvinylidene fluoride (PVDF) membrane. Such inherently hydrophobic membrane can be rendered hydrophilic by applying or otherwise treating the surface thereof with a hydrophilic monomer, oligomer, or polymer.

Other materials useful as membranes include, but are not limited to, nylons and other polyamides such as Nylon 6 and Nylon 66, PTFE, polysulphones, polyethersulphones, polyarylsulphones, nitrocellulose, cellulose acetate, polyolefins (such as ultrahigh molecular weight polyethylene, low density polyethylene, and polypropylene), thermoplastic fluorinated polymers (such as poly(TFE-co-PFAVE)), polycarbonates, and the like.

A typical first step in the manufacture of a membrane is casting, which provides a hydrophobic membrane with a morphological structure. This is important, since it is this hydrophobic structure which determines to a large extent the homogeneous nature of the membrane structure which is a combination of porosity and pore size. It is this structure which gives the membrane its fundamental microbial retention characteristics.

Subsequent to the initial casting, the resultant hydrophobic membrane can be rendered hydrophilic through chemical surface treatment, such as coating or grafting. Suitable processes for rendering membranes hydrophilic are known. For example, U.S. Pat. No 4,944,879, issued to M. J. Steuck on Jul. 31, 1990, describes a membrane surface treatment methodology, wherein a hydrophobic membrane is coated with one or more hydrophilic monomers, and then crosslinked onto the surface of the membrane and its pores, rendering hydrophilic the coated and crosslinked regions of the membrane. U.S. Pat. No. 5,928,792, issued to W. Moya on Jul. 27, 1999, describes another surface treatment methodology, wherein a hydrophilic perfluorocarbon copolymer composition is provided onto a hydrophobic membrane formed from PTFE and other fluorinated resins.

Regardless of the variety of processes available, in practice of the present invention, it is preferred that the "hydrophilization" process employed should simply render the initially cast membrane sufficiently hydrophilic for use in aqueous filtration, without changing, modifying, or otherwise altering the pore size, membrane structure, hydrophobic bubble point, or microbial retention characteristics of the base membrane.

Several good base membranes are available. One such membrane is sold as DURAPORE® PVDF membrane by Millipore Corporation of Bedford, Mass. Another useful base membrane is a PTFE membrane sold as QUICK-CHANGE® membrane by Millipore Corporation.

When employing naturally hydrophobic membrane, such as PTFE or PVDF, it is preferred—especially in the pleated format discussed further below—that only portions or regions of the membrane be rendered hydrophilic. This may be accomplished, for example, by covering in the course of hydrophilization those areas or regions which should remain hydrophobic with a removable mask made of, for example, MYLAR® films, glass, metal plates, or other sufficiently impermeable materials.

The utilization of the differentiated membrane regions according to present invention in a common barrier filter device, among other things, ensure that both filter membranes can be operated within their appropriate pressure ranges, in particular, there will be little or no chance for the sterilizing grade phobic membrane to be pressurized beyond its intrusion pressure, risking breach thereof, as the hydrophilic membrane—though wet—provides a highly permeable path for the release of excess gas. In essence, the permeability of the hydrophilic membrane provides an upper limit for the amount of gaseous pressure that can accumulate within the barrier filter.

Although the inventive multi-functional filter unit can be employed in several different applications, in a preferred application, it is installed as an aseptic barrier filter in a chemical process system for the manufacture of a liquid product from a liquid raw material, wherein such manufacture requires membrane-based filtration of said liquid raw material. Broken down into certain of its basic constituent parts—as shown schematically in FIG. 4, the chemical process system 100 comprises, the barrier filter unit 10 a network of conduits and receptacles 20 that essentially defines the system's fluid process stream; the process membrane 60, end a receptacle 30 for collecting finished product.

The network of conduits and receptacles 20—as evident from the various embodiments illustrated in FIGS. 5 to 9—is subject to a broad range of differing configurations. Despite the variety. In all embodiments of the inventive system, network 20 will junction to receive liquid raw and/or starting material at "one end", conduct it through the process stream defined thereby, and produce the desired liquid product at the "other end". To effect such functionality, the network 20 is provided with (a) input means for introducing said liquid raw material into said fluid process stream, and (b) output ports for discharging fluid out of said fluid process stream. The network 20 is preferably an "essentially closed" network, and also, preferably sterile and/or aseptic.

In all but the simplest embodiments of the inventive system, the input means will typically include both liquid inlet 40 and gas inlets 50. It is possible also to employ a single common inlet capable of receiving both liquid and gaseous material.

The network 20 employs at least two discharge ports 22 and 24. The first discharge port 22 enables discharge of finished product from the network 20 into a product collection receptacle 30. The second discharge port 24 enables discharge of a fluid stream—either liquid or gas—from the network 20 into the sterile barrier filter 10. To allow integrity testing of process membrane 60, without interfering with product collection at port 22, the second discharge port 20 is located along the fluid process stream at a position between the process membrane 60 and port 22.

The product collection receptacle 30 is essentially any receptacle capable of holding the predetermined product yield capacity of the system 100. Preferably, the receptacle will be provided with the appropriate fittings necessary to establish a tight, hermetically sealed union with system's first discharge port 22, thereby maintaining the system's aseptic and/or sterile condition. The receptacle can be made in any shape and of virtually any material (e.g., glass, plastic, or metal), provided of course, said material is compatible with the product sought to be collected.

In the inventive system, two membrane components are utilized. The membrane component's are functionally different. Care should be taken not to confuse the two. The "filter membrane" component 12 is that employed within the barrier filter 10. The "process membrane" component 60 is that employed in the system 100 for the purpose of conducting the system's chemical manufacturing process. The chemical process will yield product with or without the "filter membrane" component 12. The chemical process will either not yield the desired product or otherwise yield a markedly different product (i.e., in respect of purity, concentration, end the like) in the absence of the "process membrane" component 60. Also, in accordance with the present invention, the filter membrane component 12 must be provided with substantially differentiated hydrophobic and hydrophilic regions. There is no such requirement for the process membrane component 60. Rather, the present invention requires only that the process membrane component 60 be positioned within said fluid process stream and be capable of filtering the aforementioned liquid raw material as it passes therethrough.

Material useful for the manufacture of the process membrane component 60 include synthetic or natural compositions and may be inorganic, organic, or mixture thereof. Typical inorganic materials include, but are not limited to, glasses, ceramics, metals, cermets (i.e., ceramic/metal composites), and the like. The organic materials are generally polymeric in nature, and can be substituted or unsubstituted. Typical polymers include, but are not limited to, polysulfones; polystyrenes, including styrene-containing copolymers such as acrylonitrile-styrene copolymers, styrene-butadiene copolymers and styrene-vinylbenzylhalide copolymers; polycarbonates; cellulosic polymers, such as cellulose acetate-butyrate; cellulose propionate, ethyl cellulose, methyl cellulose, nitrocellulose, etc.; polyamides and polyimides, including aryl polyamides and aryl polyimides; polyethers; poly(arylene oxides) such as poly(phenylene oxide) and poly(xylylene oxide); poly (esteramide-diisocyanate); polyurethanes; polyesters (including polyarylates) such as poly(ethylene terephthalate), poly(alkyl methacrylates), poly(alkyl acrylates), poly(phenylene terephthalate), etc.; polysulfides; poly(siloxanes); polymers from monomers having the alpha-olefinic unsaturation other than mentioned above such as poly(ethylene), poly(propylene), poly(butene-1), poly(4-methyl pentene-1), polyvinyls, e.g., poly(vinyl chloride), poly(vinyl fluoride), poly(vinylidene chloride), poly (vinylidene fluoride), poly(vinyl alcohol), poly(vinyl esters) such as poly(vinyl acetate) and poly(vinyl propionate), poly(vinyl pyridines), poly(vinyl pyrrolidones), poly(vinyl ethers), poly(vinyl ketones), poly(vinyl aldehydes) such as poly(vinyl formal) and poly(vinyl butyral), poly(vinyl amides), poly(vinyl amines), poly(vinyl phosphates), and poly(vinyl sulfates); polyallyls; poly(benzobenzimidazole); polyhydrazides; polyoxadiazoles; polytriazoles; poly (benzimidazole); polycarbodiimides; polyphosphazines; etc., and interpolymers, including block interpolymers containing repeating units from the above and grafts and blends containing any of the foregoing. Typical substituents include halogens; such as fluorine, chlorine and bromine; hydroxy groups; lower alkyl groups; lower alkoxy groups; monocyclic aryl; lower acyl groups; and the like.

Methods for the manufacture of membranes for the process membrane component 60 are well documented, for example, in the patent literature. See e.g., U.S. Pat. No. 5,217,802, issued to L. Scarmoutzos on Jun. 8, 1993; U.S. Pat. No. 5,037,457; U.S. Pat. No. 4,954,256, issued to P. Degen on Sep. 4, 1990; U.S. Pat. No. 5,037,457, issued to P. Goldsmith et al. on Aug. 6, 1991; and U.S. Pat. No. 5,554,414, issued to W. Moya et al. on Sep. 10, 1996.

Attention is now directed to certain representative product and system embodiments of the present invention.

In FIG. 1, a filter unit is shown comprising, in a common enclosure (not shown), a plurality of hydrophilic membrane discs 12A, 12B and 12C stacked together with a hydrophobic membrane disc 13 inserted between hydrophilic membranes 12A and 12B. In this particular assembly, the preferred hydrophobic and hydrophilic membrane discs are Durapore® membrane discs. These are PVDF-based membranes available form Millipore Corporation.

Figure 2:
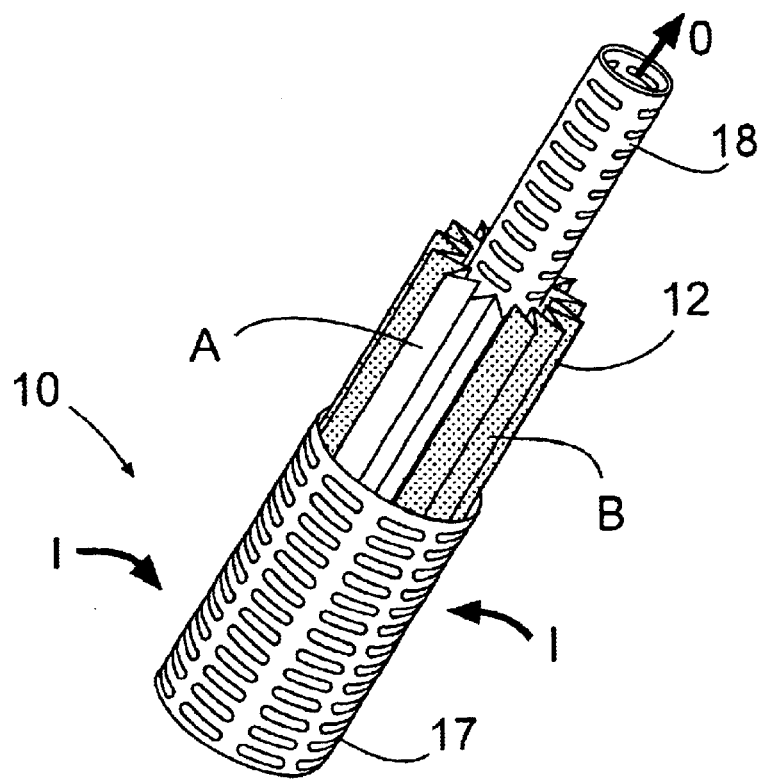
FIG. 2 is an isometric view, partially in section, of a pleated filter with alternating vertical hydrophobic and hydrophilic regions in accordance with one embodiment of the present invention.
Figure 3:
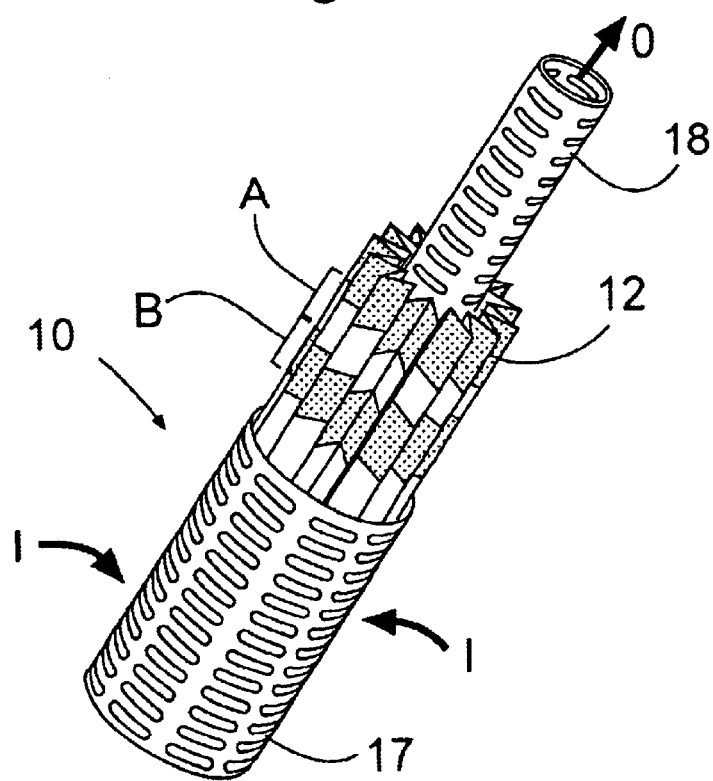
FIG. 3 is an isometric view, partially in section, of a pleated filter with alternating horizontal hydrophobic and hydrophilic regions in accordance with one embodiment of the present invention.

FIGS. 2 and 3 show embodiments of the present invention that implement, within a well-known filter cartridge format, a single tubular pleated membrane sheet 12 having differentiated regions of hydrophobicity (A) and hydrophilicity (B). The single tubular pleated sheet 12 is maintained in its relatively fixed tubular conformation within the filter cartridge 10 by use of external and internal supports 17 and 18. Supports 17 and 18 are made of rigid material and provided with uniformly dispersed holes to allow the inward flow (I) of fluid from regions peripheral to the membrane 12, then through membrane 12 into the filter cartridge 10's core, and then outwardly (O) therefrom. Filter cartridge 10 (in both the FIG. 2 and FIG. 3 embodiments) is provided with an external sleeve (i.e., the "common enclosure", not shown) equipped with and inlet and outlet. The inlet leads into the said peripheral regions. Said core leads into the outlet.

Although the external sleeve of the filter cartridges 10 in FIGS. 2 and 3 are not shown, reference can be made to FIGS. 5, 6, 7, and 8 for schematic illustration of several examples of suitable common enclosures 19.

In respect of the manufacture of supports 17 and 18, polypropylene material sold under the tradename TYPAR® (available from E.I. du Pont de Nemours and Company of Wilmington, Del.) yields a satisfactory product. While there is no criticality to the structural configuration of supports 17 and 18, an open mesh structure is preferred to assist in the removal of water that may become trapped against hydrophobic membrane regions and consequently frustrate gas flow during, for example, integrity testing. This allows the membrane to be dry or substantially water free, especially in the hydrophobic areas, which allows for the rapid passage of gases through the hydrophobic areas at relatively low pressures, as they do not need to displace any residual water that may be on the membrane surface or contained within the membrane pores.

The size of openings can vary widely and should be sufficient to support the membrane while allowing water on the membrane surface or in the membrane pores to be substantially drained from the membrane at least in the hydrophobic areas. Suitable open mesh materials include plastic screening and extruded open netting such as NAL-TEX® netting available from U.S. Netting of Austin, Tex.

Although both pleated sheet configuration in FIGS. 2 and 3 use only a single membrane sheet, other pleated sheet configurations can use a plurality of pleated membrane sheets, each sheet being individually either hydrophobic or hydrophilic. Each sheet can individually form a pleated tube, with the tubes being co-axially inserted one into the other. Or—as shown in FIG. 9—each sheet can define one arcuate aide of a single pleated tube.

Figure 9:
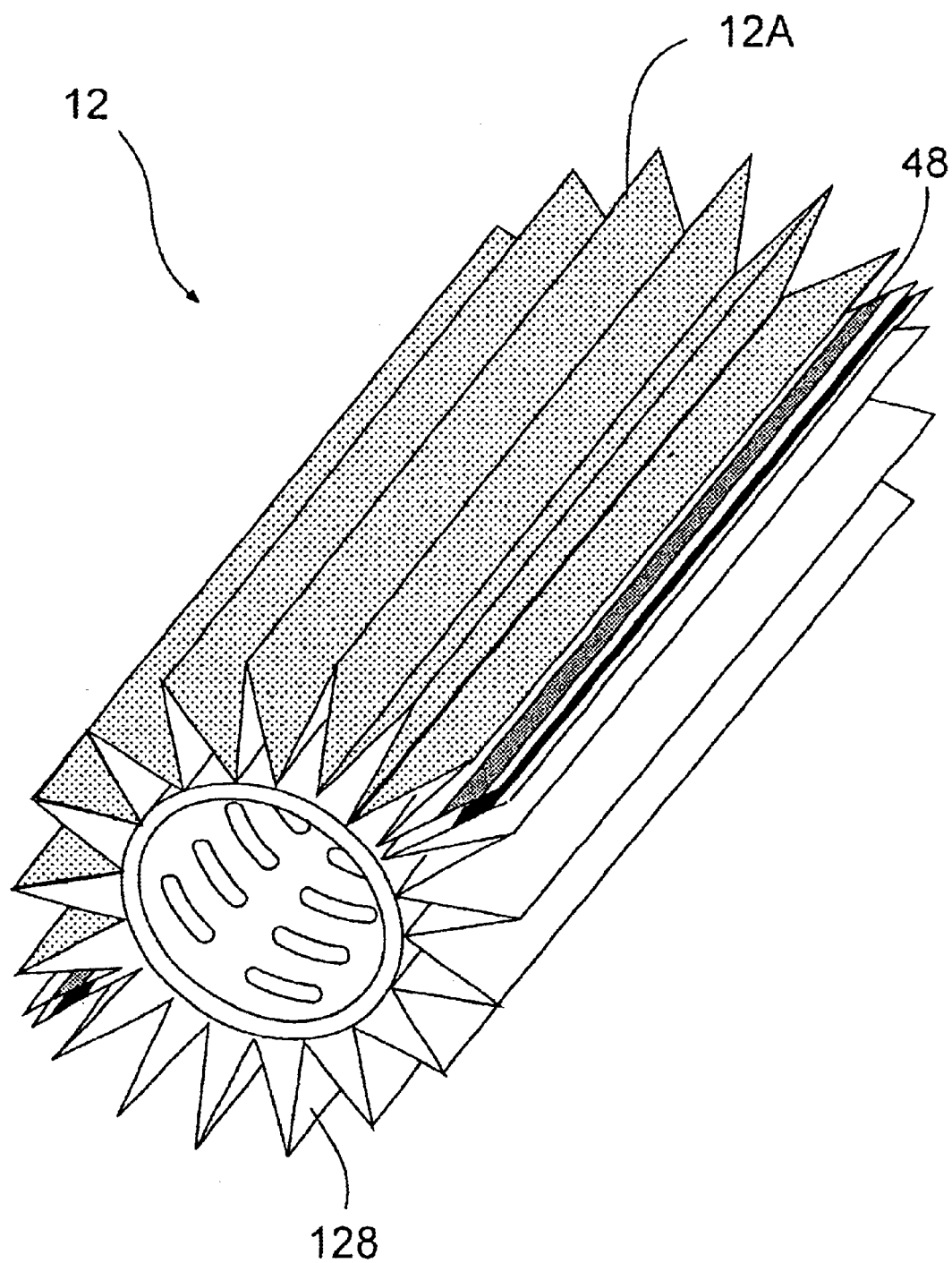
FIG. 9 is an isometric view of an embodiment of a membrane assembly useful in the present invention.

More particularly, in FIG. 9, there is illustrated a tubular pleated membrane configuration 12 comprising a plurality of individual membrane sheets 12A and 12B, at least one of which is hydrophilic (e.g., membrane 12A), with another being hydrophobic (e.g., membrane 12B), sealed together to form a structure of the present invention. In one desirable configuration, hydrophilic membrane 12A is a Durapore® membrane (available from Millipore Corporation) and hydrophobic membrane 12B is a stretched PTFE membrane (e.g., such as made by and available form W.L. Gore and Associates of Wilmington. Del.). A hydrophilized Durapore® membrane can also be utilized. Membrane sheets 12A and 12B are each individually pleated, then joined to each other, in this case by a strip of adhesive 48.

Suitable adhesives include those which are compatible with each membrane layer and are typically a melt bond type of adhesive such as a polyolefin, including polyethylene, polypropylene and the like or a PTFE resin. Some combinations of membranes can simply be heat sealed or ultrasonically sealed together especially when they are formed of the same polymer and one or both contains a surface treatment rendering them respectively hydrophilic and hydrophobic.

It will be appreciated that the filter unit of the present invention—owing in large part to the combined usage of hydrophilic and hydrophobic membrane material therein—can be conveniently steam sterilized in place (i.e., without removing it from the system into which it is installed), and hence, enabling better control and maintenance of extant aseptic conditions.

After conducting such in situ steam sterilization (a.k.a., "steam-in-place" or "SIP"), it has been found desirable to maintain system integrity by establishing a positive pressure using air or other suitable gas during the subsequent cooling period. If a dry product filter and system are required, the gas must bleed from the upstream and downstream condensate points until the system is dry and cooled to operating temperature. The use of the filter unit 10 of the present invention allows for a free flow of gas through the hydrophobic regions of the membrane for the cooling process, and the draining of the condensate through the hydrophilic regions of the membrane.

Because autoclaving end steam-in-place procedures can damage a filter, sterilized filter units are often integrity tested prior to their use. Post-sterilization integrity testing typically involves wetting the product filter with a standard wetting medium or other liquid (e.g., the liquid raw material). This can result in breaching sterility of the sterilized system. Water used to wet the filter prior to integrity testing cannot be drained downstream of the dosed filter system, and will remain in the sterile product tank. In situations where this is unacceptable, such as where dilution or immiscibility issues are present, the sterile barrier filter of the present invention will allow the water used to integrity test the System to be drained from the system without breaking the sterile barrier. By the appropriate placement and use of valves, the sterile product filter can be wet with liquid, usually water, which is than routed to the sterile barrier filter. Air is evacuated through the hydrophobic portion of the membrane; water through the hydrophilic portion.

A further advantage of the sterile barrier filter of the present invention is realized during enhanced bubble point integrity testing of the product filter. The diffusion of the test gas through the wet product filter membrane will create a back pressure downstream of the product filter if the system is not vented to atmospheric pressure. This situation will lead to errors in determination of the bubble point. Use of the sterile barrier filler allows for free flow of the test gas to maintain the downstream side of the filter at the required atmospheric pressure. Once integrity testing of the sterilizing product filter is complete, all water downstream of the sterilizing filter can be blown through the sterile barrier filter. This filter is then isolated with the appropriate valving and aseptic processing can be executed. Following the process, the sterile barrier filter is dismantled from the line and bubble tested off-line, using an isopropyl alcohol/water (70/30%) mixture as the wetting medium.

Figure 5:
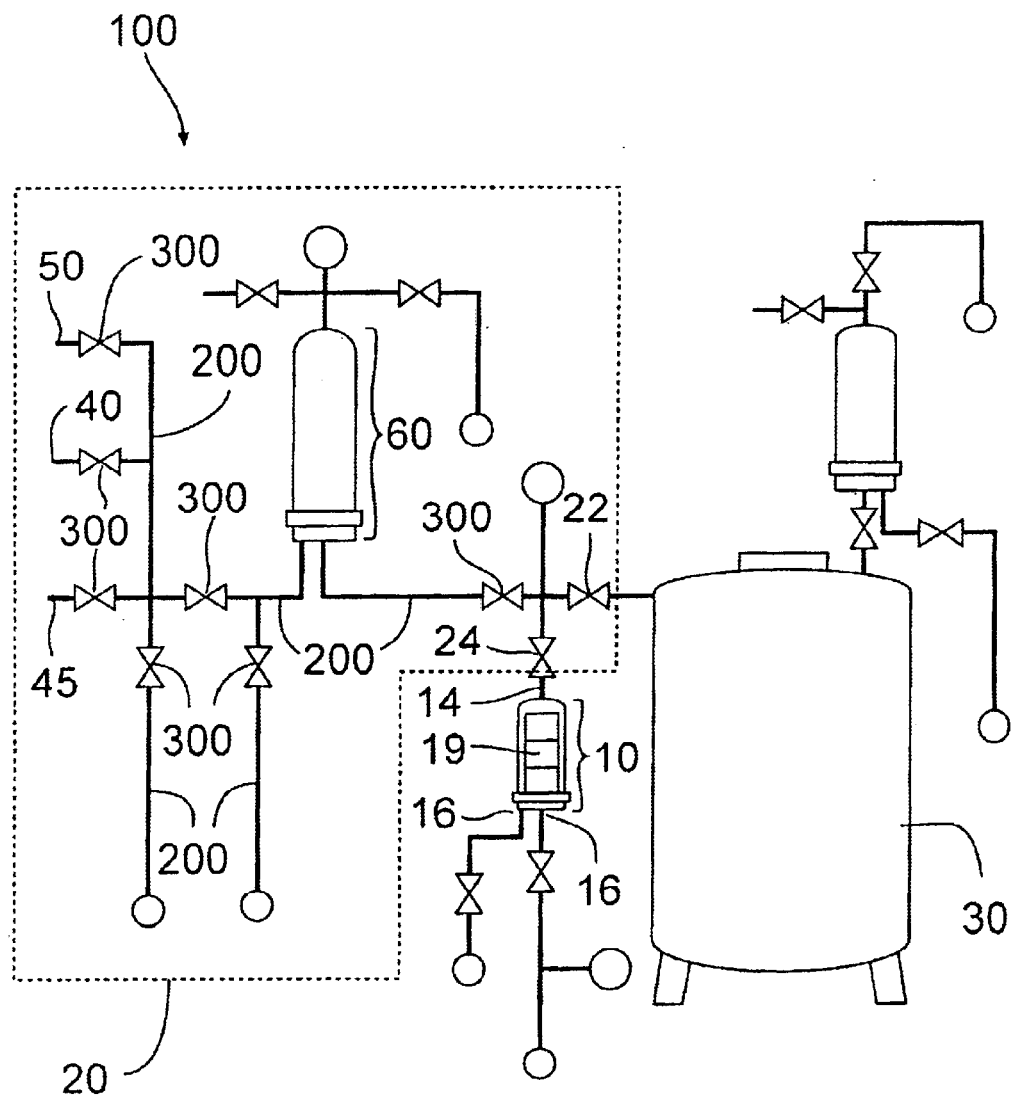
FIG. 5 is a schematic diagram of an embodiment of the chemical processing system illustrated in FIG. 4.

FIG. 5 illustrates an embodiment of a chemical process system 100 according to the present invention, utilizing barrier filter 10. The chemical process system 100 comprises a product collection vessel 30, the barrier filter 10, and a network or conduits and receptacles 20. In this particular embodiment, network 20 comprises conduits 200, a receptacle (cf., component 60), and valves 300, arranged to define a fluid process stream. At its upstream end, the network is provided with inlets 40, 50, and 45 for the introduction into the fluid process stream of gas, water, and steam. At its downstream end, the network is provided with discharge ports 22 and 24.

Discharge port 22 enables the transit of fluid out of network 20 and into product collection vessel 30. Discharge port 24, coupled to the filter inlet 14, enables the transit of fluid (liquid or gaseous) out of network 20 and into barrier filter 10.

In one mode of integrity testing the chemical process system 100 of FIG. 5, a mixture of air and nitrogen gas in introduced into the system through inlet 40, water through inlet 50, and steam though inlet 45. After passing through the receptacle 60—i.e., a process filter unit containing a process filter membrane—the water, nitrogen, air, and steam continue through conduits 200 and ultimately into the barrier filter 10, where each is respectively discharged through barrier filter outlets 16.

More particularly, to integrity test filter 60, after flowing steam through the entire system 100, water is dispensed from inlet 50 through process filter unit 60, then through valve 24, then through barrier filter unit 10. Valve 22 is closed throughout the procedure. Next, air or nitrogen gas is dispensed through the system 100 through inlet 40 through process filter unit 60 at a pressure below the process filter unit 60's so-called "bubble point". Because the process filter unit 60 is wet from the preceding step, it will not pass any bulk volume of gas, thus enabling the acquisition of integrity-characterizing measurements of pressure decay on the feed side of filter 60. When the air or nitrogen gas enters the system 100, it will urge water throughout the system to exit through the barrier filter 10. And, once the integrity test is complete, the fluid to be processed can now pass through process filter unit 60 and through valve 22 (now open) into the collection vessel 30.

Upon completion of integrity testing, barrier filter 10 can be isolated from the remainder of the system 100 by activating or deactivating the appropriate valves 300 such that the flow proceeds from the product filter/receptacle 60 to the product collection vessel 30.

Figure 8:
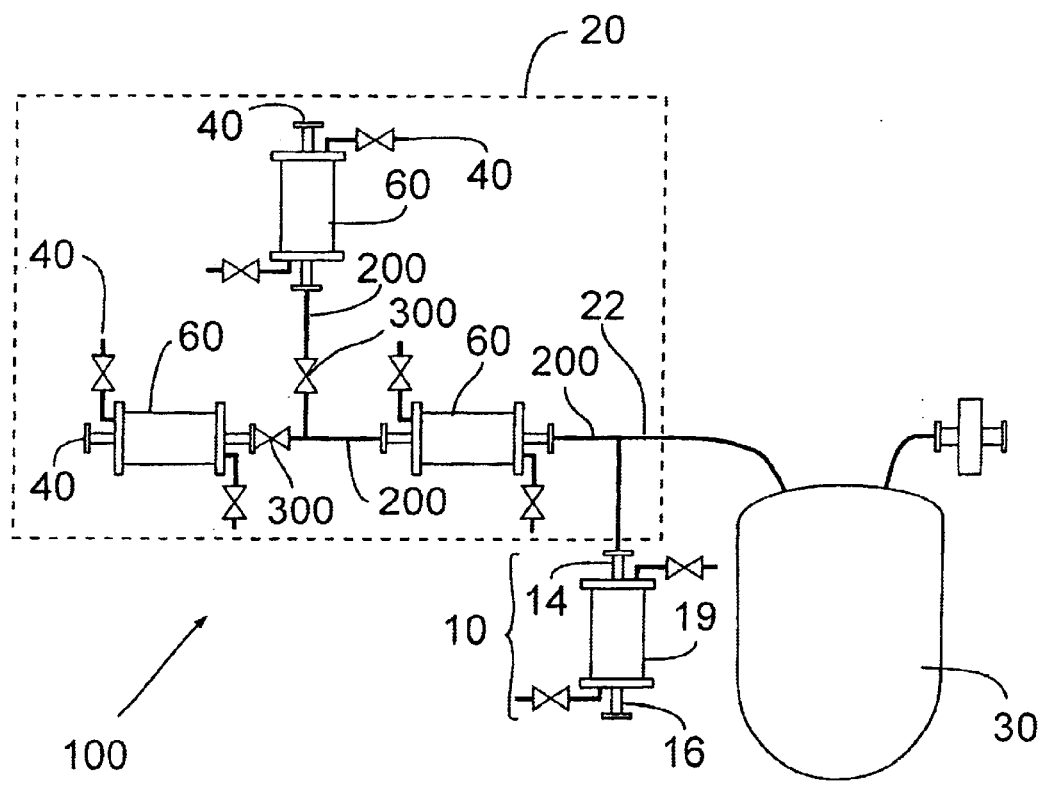
FIG. 8 is a schematic diagram of still another embodiment of the chemical processing system illustrated in FIG. 4.

FIG. 8 illustrates another embodiment of a chemical process system 100 according to the present invention, utilizing barrier filter 10. The chemical process system 100 of FIG. 8 comprises a product collection vessel 30, the barrier filter 10, and a network of conduits and receptacles 20. In this particular embodiment, network 20 comprises conduits 200, a receptacle (cf., component 60), and valves 300, arranged to define a fluid process stream. At its several upstream ends, the network is provided with inlets 40 for the introduction into the fluid process stream of gas, water, and/or steam. At its downstream end, the network is provided with discharge ports 22 and 24 (valves not shown).

Notable in the embodiment of FIG. 8 is the use of a bag as the product collection vessel 30. Such systems are often used in connection with the processing, collection, and/or packaging of intravenously-administered fluids (e.g., blood serum), thus calling for heightened vigilance in sterilization and septic maintenance. While process filter units 60 are indispensable for processing the collected fluid, they may also be a source of leechable extractable material. Gamma irradiation of the system 100—a common sterilization procedure implemented with such systems—can increase the level of readily leechable extractable material. This is problematic. In many cases the "bags" have a comparatively low volume capacity and the level of extractables can be considerable. Regardless, use of the inventive barrier filter 10 enables any sterile process filter units 60 attached to the bags to be both flushed to reduce extractable content and then integrity tested without jeopardizing the extant sterility of such closed sterile system.

Also notable in FIG. 8 is the use of simple conduits, rather than valves, for discharge ports 22 and 24. The present invention is not limited to any configuration for such discharge ports. Any means capable of providing fluid access from the system into the barrier filter and into the product collection vessel will suffice. A conduit will provide such functionality.

Figure 4:
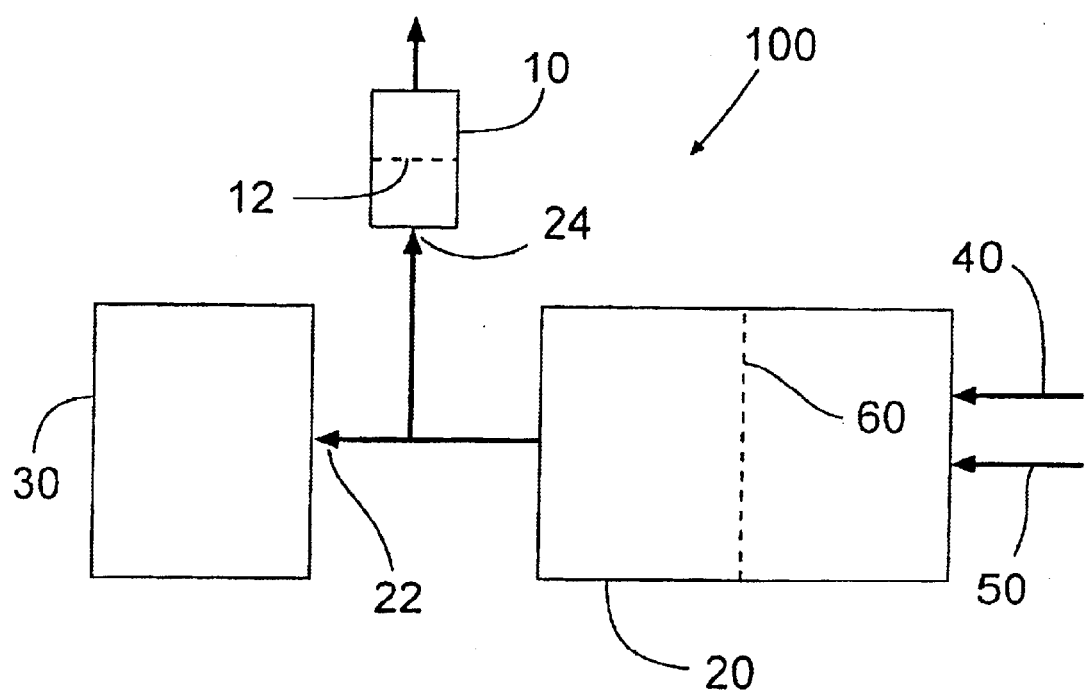
FIG. 4 is a schematic illustration of a chemical process system according to the present invention.

Although the embodiments illustrated in FIG. 8 and FIG. 5 are in accord with the basic system illustrated in FIG. 4, the applications of the inventive filter unit 10 are not limited to said basic system. The inventive filter unit 10 can be employed in virtually any membrane-based fluid system, wherein integrity testing (involving both gaseous and liquid fluids) of the system's process membrane is desired. Examples of such systems (i.e., systems 110) are represented in FIGS. 6 and 7.

Figure 6:
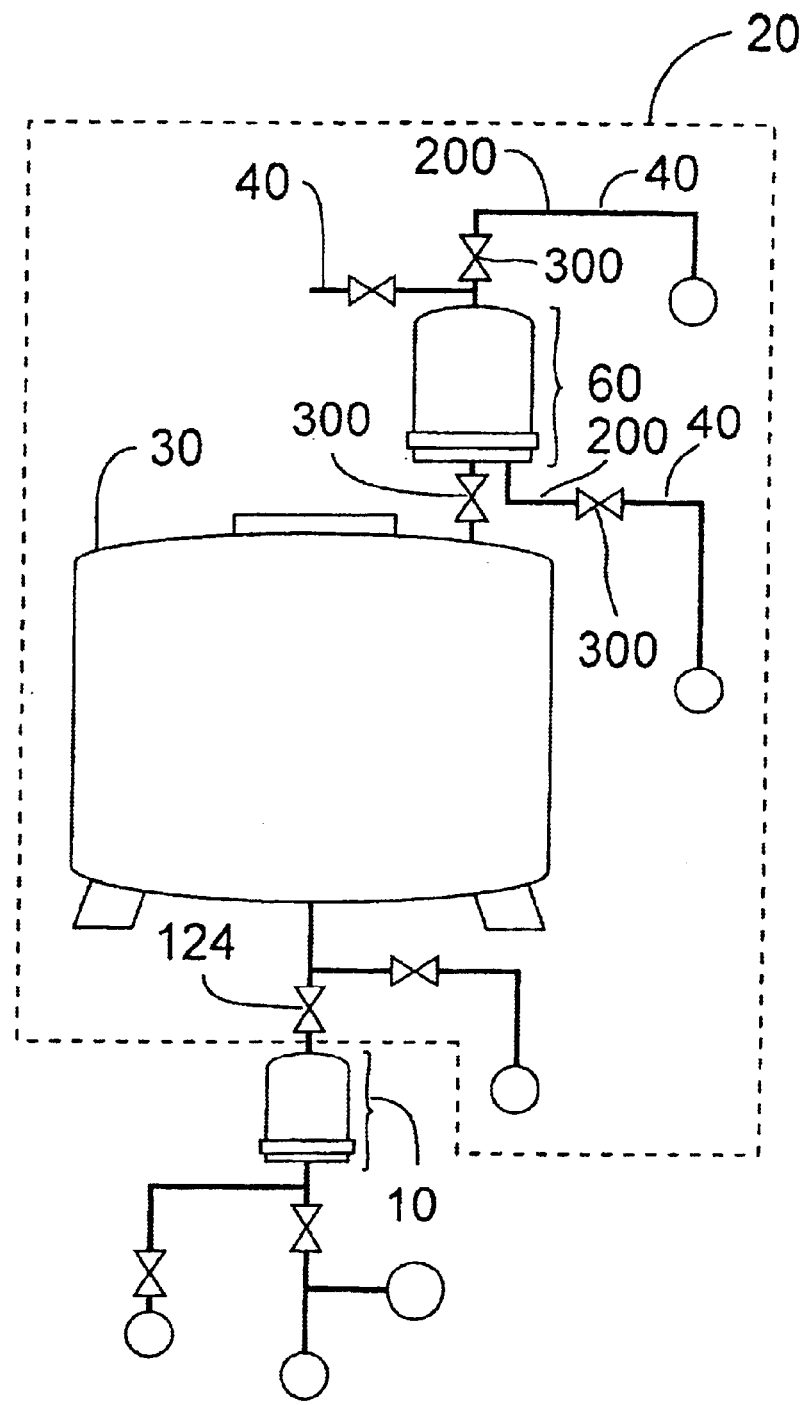
FIG. 6 is a schematic diagram of another embodiment of the chemical processing system illustrated in FIG. 4.
Figure 7:
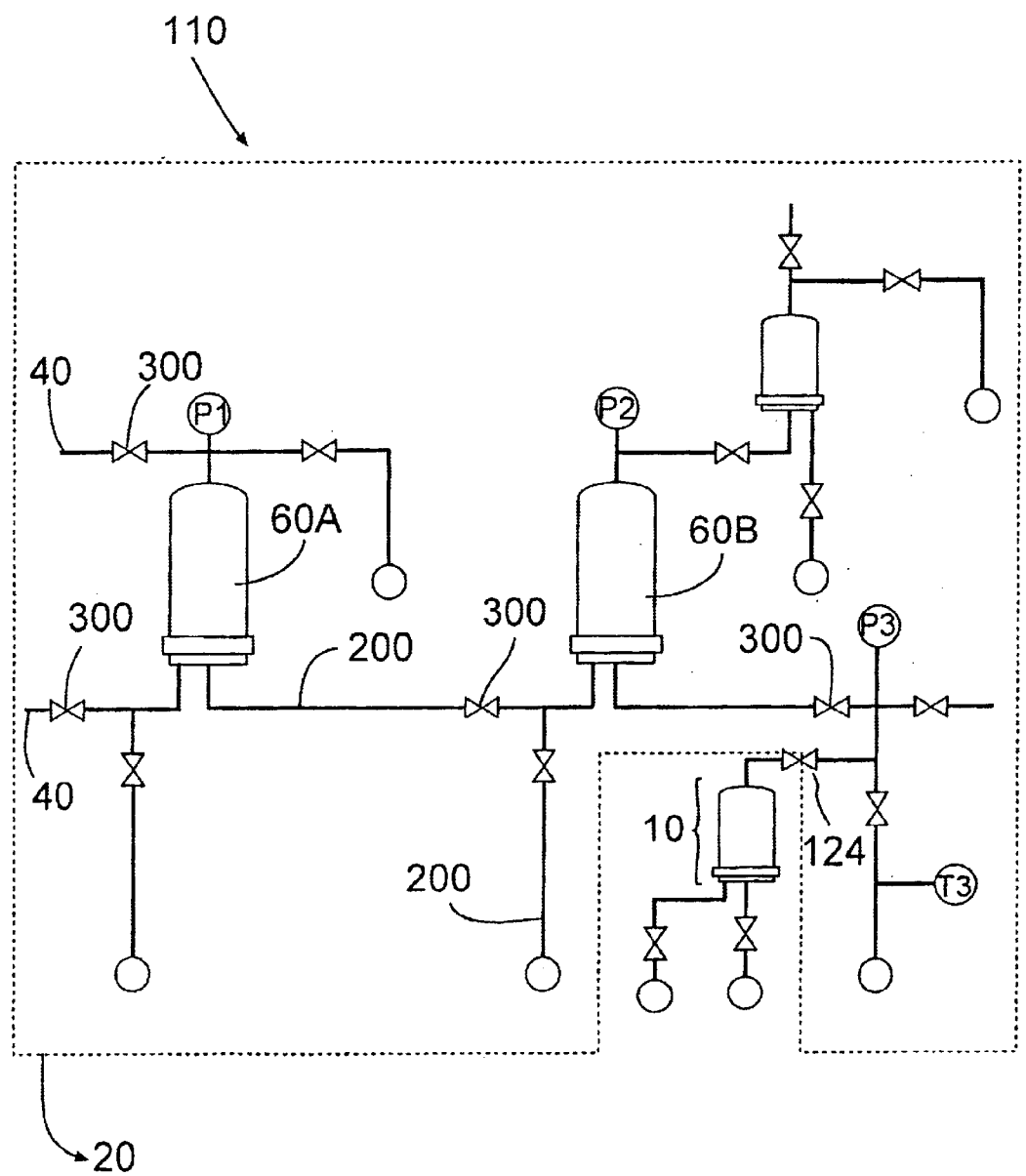
FIG. 7 is a schematic diagram of still another embodiment of the chemical processing system illustrated in FIG. 4.

The systems 110 of FIG. 6 and 7 are similar to systems 100 of FIGS. 4, 5, and 8 in that they all implement a network of conduits and receptacles 20. System 110 differ in the reduced emphasis of a product collection vessel and its functionality, particularly in respect of the positioning of the filter unit 10. Essentially, if a product collection vessel is implemented—as is the case in FIG. 6—for purposes of construing the scope of the invention, it is considered part of the network of conduits and receptacles 20.

FIG. 6 illustrates a system 110, wherein a sterile barrier filter 10 is positioned in communication with a drain 124 (i.e., system discharge port 124) of a sterile tank 30 to allow the draining of condensate, cooling, and drying, subsequent to the conduct of, for example, steam-in-place sterilizing procedures.

In particular, system 110 of FIG. 6 comprises a membrane-based network of conduits and receptacles 20, the network 20 having a system discharge port 124 leading into the installed barrier filter 10. In this particular embodiment, network 20 includes conduits 200, receptacles (cf., components 60 and 30), and valves 300, arranged to define a fluid process stream. Component 30 is essentially a vat used to collect the permeate passed through component 60. Component 60 is a process filter unit, in which is housed a process membrane. The network 20 is provided with inlets 40 at its several upstream ends for the introduction into the fluid process stream of gas, water, and/or steam.

Practitioners will appreciate that certain fluid separation procedures, particularly those calling for heightened vigilance in maintaining aseptic performance, often benefit from the use of redundant process filters. For such "low-tolerance" procedures, capability to test in situ the integrity of each process filters is highly desirable. This, however, is difficult to achieve.

When two redundant process filters (cf., process filter 60A and 60B in FIG. 7) are subjected to pre-process integrity testing and/or sterilization, it is often difficult to test both filter units adequately without having to disengaging any conduit(s) linking the redundant filters and thus compromising sterility. In particular, the first of the two redundant filters (60A) can be easily wetted and tested, and the second filter (60B) can be easily wetted through the first filter. However, because of their sequential arrangement, it is difficult to get the gas (e.g., air) to pass unhindered by the now wet first filter, to apply pressure to the second filter.

As shown in FIG. 7, a bi-directional barrier filter 10 is positioned downstream of the second of the redundant filters 60B to enable the wetting liquid downstream of the second filter 60B to be evacuated from the system without compromising the sterility of the system. The integrity test, which is a gas flow-based operation, in conducted through this sterile barrier filter 10.

While the present invention has been discussed in reference to certain particular embodiments thereof, those skilled in the art, having the benefit of the teachings of the present invention set forth herein can effect numerous modifications thereto. These and like modifications are to be construed as being encompassed within the scope of the present invention as set forth in the appended claims.

What is claimed is:

1. A membrane-based filtration system comprising:
   a network defining a fluid process stream, wherein (a) said network has at least one entry port for introducing fluid into said fluid process stream and at least one discharge port for discharging fluid out of said fluid process stream, and (b) a product collection vessel, said at least one fluid discharge port being provided on said product collection vessel;
   a process membrane positioned within said fluid process stream upstream of said product collection vessel, said membrane capable of filtering liquid passing therethrough; and
   a barrier filter installed at said at least one said fluid discharge port, said barrier filter comprising, within a common enclosure, a single pleated membrane having alternating bars of said hydrophilic and hydrophobic regions.

2. The filter of claim 1, wherein said bars are arranged substantially orthogonal to the pleats of said single pleated membrane.

3. The filter of claim 1, wherein said bars are arranged substantially parallel to the pleats of said single pleated membrane.

4. A membrane-based filtration system comprising:
   a network defining a fluid process stream, wherein (a) said network has at least one entry port for introducing fluid into said fluid process stream and at least one discharge port for discharging fluid out of said fluid process stream, and (b) a product collection vessel, said at least one fluid discharge port being provided on said product collection vessel;
   a process membrane positioned within said fluid process stream upstream of said product collection vessel, said membrane capable of filtering liquid passing therethrough; and
   a barrier filter installed at said at least one said fluid discharge port, said barrier filter comprising, within a common enclosure, a stack of several non-contiguous independent filter membranes, each of said filter membranes being either hydrophilic or hydrophobic, the hydrophilic membranes being interspersed between the hydrophobic membranes, and wherein the common enclosure is a substantially cylindrical tube and said membranes are circular, and said hydrophilic membranes and said hydrophobic membranes are arranged in said stack in a uniformly alternating pattern.

5. A chemical process system for the manufacture of a liquid product from a liquid raw material, wherein said manufacture requires membrane-based filtration of said liquid raw material, and wherein the chemical process system comprises:
   a network defining a fluid process stream, said network having means for introducing said liquid raw material into said fluid process stream, said network having ports for discharging fluid out of said fluid process stream;
   two process membranes positioned within said fluid process stream, said membranes capable of filtering said liquid raw material as said material passes therethrough; and
   a barrier filter installed at one of said fluid discharge ports, the barrier filter comprising, within a common enclosure, a stack of several non-contiguous independent filter membranes, each of said filter membranes being either hydrophilic or hydrophobic, the hydrophilic membranes being interspersed between the hydrophobic membranes, and wherein the common enclosure is a substantially cylindrical tube and said membranes are circular, and said hydrophilic membranes and said hydrophobic membranes are arranged in said stack in a uniformly alternating pattern;
   wherein (a) said two process membranes are positioned within said fluid process stream such that the second of said two process membranes is redundant of the first of said two process membranes; and (b) the fluid discharge port at which said barrier filter is installed is located downstream of both said first and said second of said process membrane.

6. A chemical process system for the manufacture of a liquid product from a liquid raw material, wherein said manufacture requires membrane-based filtration of said liquid raw material, and wherein the chemical process system comprises:
   a network defining a fluid process stream, said network having means for introducing said liquid raw material into said fluid process stream, said network having ports for discharging fluid out of said fluid process stream;
   two process membranes positioned within said fluid process stream, said membranes capable of filtering said liquid raw material as said material passes therethrough; and
   a barrier filter installed at one of said fluid discharge ports, the barrier filter comprising, within a common enclosure, a single pleated membrane having alternating bars of said hydrophilic and hydrophobic regions
   wherein (a) said two process membranes are positioned within said fluid process stream such that the second of said two process membranes is redundant of the first of said two process membranes; and (b) the fluid discharge port at which said barrier filter is installed is located downstream of both said first and said second of said process membrane.

7. The chemical process system of claim 6, wherein said bars are arranged substantially orthogonal to the pleats of said single pleated membrane.

8. The chemical process system of claim 6, wherein said bars are arranged substantially parallel to the pleats of said single pleated membrane.

* * * * *